United States Patent [19]

Becht

[11] 4,109,844

[45] Aug. 29, 1978

[54] SURGICAL STAPLING INSTRUMENT

[75] Inventor: Carl T. Becht, Cincinnati, Ohio

[73] Assignee: Senco Products, Inc., Cincinnati, Ohio

[21] Appl. No.: 742,843

[22] Filed: Nov. 18, 1976

[51] Int. Cl.$^2$ .............................................. B25C 5/02
[52] U.S. Cl. .................................... 227/120; 227/19
[58] Field of Search ................ 227/19, 110, 120, 127, 227/129, 134

[56] References Cited

U.S. PATENT DOCUMENTS

| 2,874,384 | 2/1959 | Krone | 227/19 |
|---|---|---|---|
| 2,922,163 | 1/1960 | Smick | 227/110 |
| 3,638,847 | 2/1972 | Noiles et al. | 227/19 |
| 3,873,016 | 3/1975 | Fishbein | 227/19 |

*Primary Examiner*—Granville Y. Custer, Jr.

*Attorney, Agent, or Firm*—Melville, Strasser, Foster & Hoffman

[57] ABSTRACT

A surgical stapling instrument for forming and implanting a staple in the skin or fascia of a patient to close a wound or incision therein. The instrument comprises a handle portion and a nose portion. The nose portion houses a staple driver operable by an actuator pivotally associated with the handle portion. An anvil plate is affixed to the bottom of the nose portion. A plurality of staples are supported by the anvil plate and means are provided to advance the staples along the anvil plate toward the forward end thereof about which each staple is formed by the staple driver. The nose portion is also provided with a staple retaining surface spaced above the forward end of the anvil plate to minimize bending of the staple crown during the staple forming operation.

14 Claims, 29 Drawing Figures

SURGICAL STAPLING INSTRUMENT

BACKGROUND OF THE INVENTION

1. Field of the Invention

The invention relates to a surgical stapling instrument, and more particularly to such an instrument which may be of a single-use, disposable nature.

2. Description of the Prior Art

While the stapling instrument of the present invention may have many applications, it is particularly adapted for use as a surgical stapling instrument and will, for purposes of an exemplary showing, be so described. While the instrument may be so constructed as to be reusable, its nature is such that it may be readily produced as a single-use, disposable instrument and again will be so described for purposes of an exemplary showing.

Recently surgeons have come more and more to the use of staples, rather than conventional thread sutures, for closing wounds or incisions in the skin and fascia of a patient. This is true largely because the use of staples is a far easier procedure and, of even greater importance, is very much faster. The use of staples substantially reduces the time required for suturing and thus the length of time the patient must be maintained under anesthesia.

Prior art workers have developed various types of surgical stapling instruments, examples of which are taught in U.S. Pat. Nos. 3,618,842; 3,643,851; 3,717,294; 3,837,555 and 3,873,016. In general, the prior art instruments are complex in construction and expensive to manufacture. The instruments do not lend themselves to a disposable construction. Prior art surgical staplers generally require a magazine or cartridge for the staples and a portion of the force required to actuate these instruments in expended in shifting a staple to an anvil means prior to the formation of the staple about the anvil means. As a result, some prior art surgical staplers require upwards of 20 pounds force to form and implant a staple.

The present invention provides a surgical stapling instrument of such simplicity that it may, if desired, be fabricated in such a way as to constitute a single-use, disposable instrument. The instrument is light weight, easy to use and requires very little force to operate it. This is true by virtue of the fact that the staples are supported by and fed along an anvil plate. No force is required on the part of the operator to shift a staple from a cartridge or magazine to the anvil about which it is formed. In addition, bending of the crown of the staple during the forming step is controlled. The surgical stapling instrument will hold more staples than those requiring a staple cartridge.

SUMMARY OF THE INVENTION

The surgical stapling instrument of the present invention comprises a handle portion and a nose portion. The nose portion is rotatable with respect to the handle portion throughout 360° so that the surgical stapling instrument may be used in various attitudes.

The handle portion is hollow and open along one edge to accommodate an actuator pivotally affixed to the handle portion. The actuator is shiftable by the operator of the instrument between a normal position wherein the actuator is located largely outside the handle portion and working position wherein the actuator is located largely within the handle portion.

The nose portion carries a cylinder which is vertically shiftable between upper and lower positions by the actuator and which is normally urged toward its upper position by spring means. A staple driver, mounted in the nose, is operatively attached to the cylinder, traveling therewith between a normal position and a staple forming position.

An anvil plate is mounted along the bottom of the nose portion and terminates at its forward end in a staple forming anvil surface. The anvil plate is so configured that it may be straddled by a plurality of staples. Spring-loaded feeder shoe means urges the staples toward the anvil forming surface. The forwardmost staple rests upon the anvil forming surface and beneath a staple retaining means which limits the amount of bending of the crown of the staple during the staple forming operation. When the actuator is shifted from its normal position to its working position, the cylinder and hence the staple driver will be shifted from their upper positions to their lower positions. Such a shifting of the staple driver will cause a staple to be implanted and formed about the anvil surface of the anvil plate with a minimum of bending of the crown portion of the staple. The very slight bending of the staple crown portion together with the constant urging of the plurality of staples toward the anvil forming surface will cause the formed and implanted staple to be readily released from the surgical stapling instrument.

It is within the scope of the invention to additionally provide a latch means in association with the handle portion and the actuator, which latch means must be unlatched before the actuator can be shifted from its normal to its working position.

BRIEF DESCRIPTION OF THE DRAWINGS

FIG. 8 is a fragmentary elevational view of the rear surface of the nose casting as seen perpendicular thereto.

FIG. 15 is a fragmentary cross sectional view taken along section line 15—15 of FIG. 2.

FIG. 28 is a front elevational view of the feeder pawl of the present invention.

FIG. 29 is a side elevational view of the feeder pawl of FIG. 28.

DESCRIPTION OF THE PREFERRED EMBODIMENTS

Figure 1:
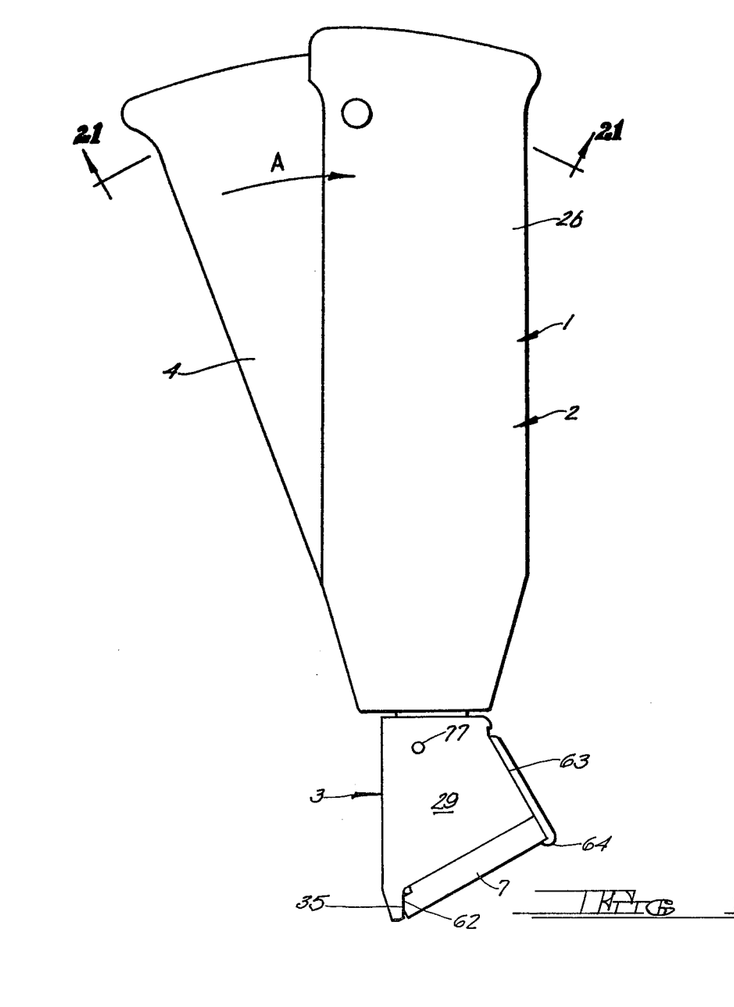
FIG. 1 is a side elevational view of the surgical stapling instrument of the present invention.
Figure 2:
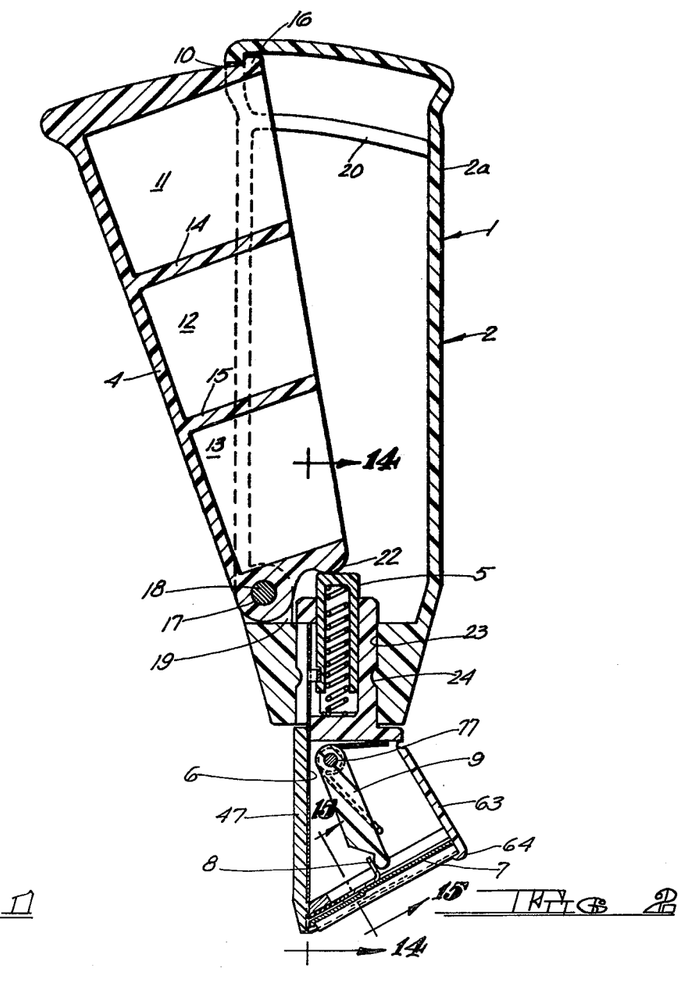
FIG. 2 is a cross sectional elevational view of the instrument.
Figure 3:
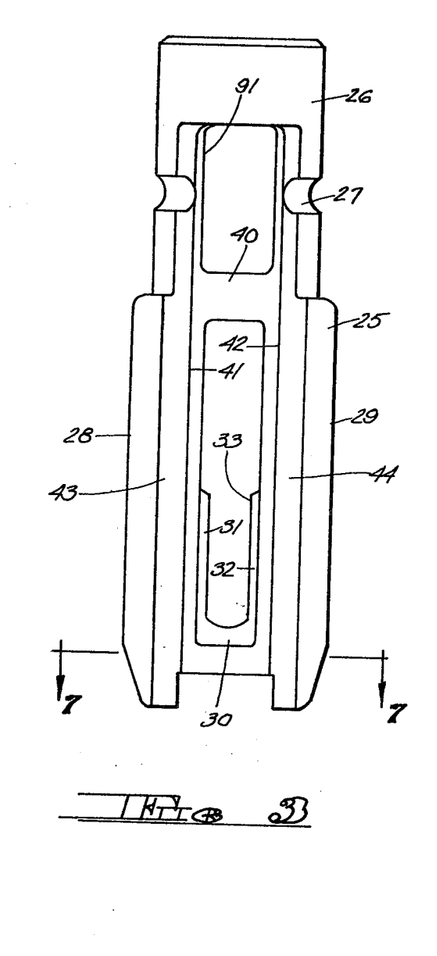
FIG. 3 is a front view of the nose casting of the present invention.

Throughout the various figures, like parts have been given like index numerals. For an initial, basic understanding of the surgical instrument of the present invention, reference is first made to FIGS. 1 and 2. The instrument is generally indicated at 1 and comprises a handle portion generally indicated at 2 and a nose portion generally indicated at 3. The nose portion 3 is captively mounted in the handle portion 1 and is preferably rotatable with respect thereto. The handle portion 1 is hollow and an actuator 4 is pivotally mounted wherein. The actuator 4 is shiftable between a normal position as shown in FIGS. 1 and 2 wherein the majority of the actuator extends outwardly of handle portion 2 and a working position wherein the majority of the actuator is located within handle portion 2. The actuator 4 cooperates with a spring loaded plunger 5 to which a staple driver 6 is operatively connected. Thus, shifting of the actuator 4 from its normal to its working position will result in the depression of plunger 5 and, as a consequence, the shifting of the staple driver 6 from a normal retracted position downwardly to a staple forming position.

The bottom end of nose portion 3 supports an anvil plate 7 which, at its forwardmost end, provides an anvil surface with which the staple driver cooperates to form a staple thereabout. A row of staples straddles and is supported by the anvil plate. The staples are urged toward the forward end of anvil plate 7 by a feeder shoe 8 which also straddles the anvil plate behind the row of staples and a cooperating, spring-loaded feeder pawl 9.

Figure 20:
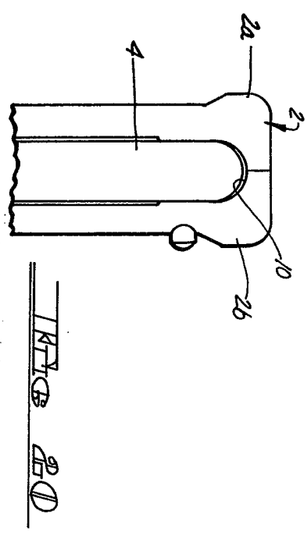
FIG. 20 is a fragmentary front elevational view of the handle portion and actuator of the surgical stapling instrument.

In the disposable version of the surgical stapling instrument of the present invention, the handle portion 2 may be made up of two halves 2a and 2b. The halves may be molded of any appropriate plastic material characterized by sufficient strength and the ability to withstand appropriate sterilization techniques. Handle halves 2a and 2b are essentially mirror images of each other and may be permanently joined together in any suitable manner including well known welding techniques applied to plastic materials. In use, the operator will grasp handle portion 2 about the body thereof with the enlarged upper end of the handle portion (see FIGS. 1, 2 and 20) extending above his hand.

Figure 23:
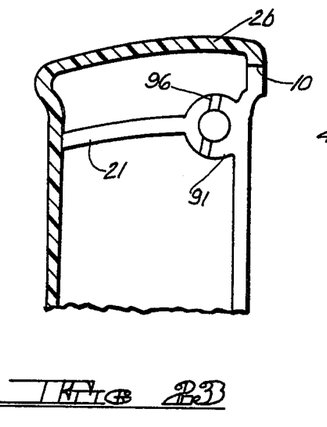
FIG. 23 is a fragmentary elevational view, partly in cross section, of the handle portion illustrating a part of the latch means of the present invention.

When the handle halves 2a and 2b are joined together, the handle portion itself is substantially hollow. Along the forward edge of the handle portion, the handle halves are so configured as to define an elongated opening 10 through which actuator 4 extends. The actuator 4 comprises an integral, one-piece, molded member which may be of the same plastic material as that used for handle halves 2a and 2b. The actuator is provided with mold cavities 11, 12 and 13 separated by integral reinforcing ribs 14 and 15 (see FIG. 2). At its upper end, the actuator has an upstanding lug 16 which will cooperate with the inside surface of handle portion 2 at the uppermost end thereof to determine the normal position of the actuator. This is illustrated in FIG. 2. At its lower end, the actuator 4 is provided with a transverse perforation 17 adapted to receive a pivot pin 18. The pivot pin 18 may be a separate member, having one end received in a bore in a boss 19 formed on the interior of handle half 2a and its other end received in a similar bore in a similar boss (not shown) formed on the inside surface of handle half 2b. Alternatively, pivot pin 18 may constitute an integral part of one of the bosses of one of the handle halves with its free end received in a bore in the boss of the other handle half. At their upper ends, handle halves 2a and 2b will have integral, internal ribs 20 and 21, respectively, (see FIGS. 2 and 23) which will guide the upper end of actuator 4, preventing lateral shifting or wobbling thereof. The lowermost end of actuator 4 has an arcuate nose 22 adapted to cooperate with plunger 5, as will be described hereinafter.

At the lower end of handle portion 2, the handle halves 2a and 2b are so configured as to provide, when assembled, a bore 23 having an annular rib 24 formed therein. The bore 23 is adapted to receive the upper end of nose portion 3 which is held therein by rib 24, as will be described hereinafter.

Attention is now directed to FIGS. 3 through 8 which illustrate the body element 25 of nose portion 3. As in the case of actuator 4 and handle portion 2, the nose body element 25 may, when the surgical stapling instrument is intended to be a single-use instrument, be molded of an appropriate plastic material, which may be the same material from which the actuator 4 and handle halves 2a and 2b are molded. The nose body element 25 has an upper portion 26 of cylindrical configuration. The portion 26 has an outside diameter so sized as to be received within the bore 23 of handle portion 2. The cylindrical portion 26 is rotatable within the bore 23 with a frictional engagement such that the nose portion 3 may be turned to any angular relationship with respect to handle portion 2 (throughout 360°), and will remain at the desired angular relationship. Cylindrical portion 26 has a groove 27 thereabout, adapted to receive the annular rib 24 of handle portion 2, rendering nose portion 3 captive with respect to handle portion 2.

Figure 4:
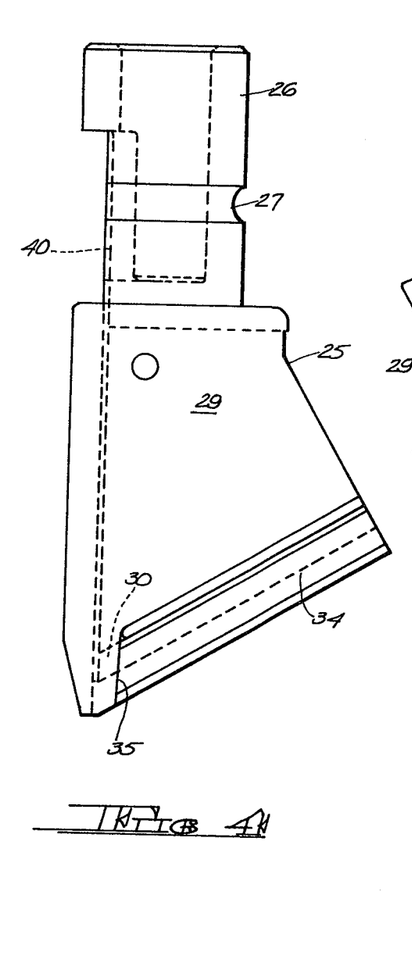
FIG. 4 is a side elevational view of the nose casting of FIG. 3.

Beneath cylindrical portion 26, the nose body element 25 comprises a pair of downwardly depending walls 28 and 29 in parallel spaced relationship. The walls 28 and 29 are joined together near the bottom front portion of nose body element 25 by an integral web 30. As is most clearly shown in FIGS. 4 and 5, the bottom edges of walls 28 and 29 slope upwardly and rearwardly. The rearward edges of walls 28 and 29 slope upwardly and forwardly while the forward edges of these walls are substantially vertical, except near the bottom where they slope downwardly and inwardly as shown in FIG. 4. Wall 28, on its inside surface, has an upwardly and rearwardly extending flange 31 which constitutes a continuation of web 30. As is most evident from FIGS. 5 and 8, the flange 31 is spaced upwardly from the bottom edge of wall 28 and extends parallel thereto. Wall 29 has a corresponding flange 32. The flanges 31 and 32 define a channel 33 therebetween.

Figures 5, 6:
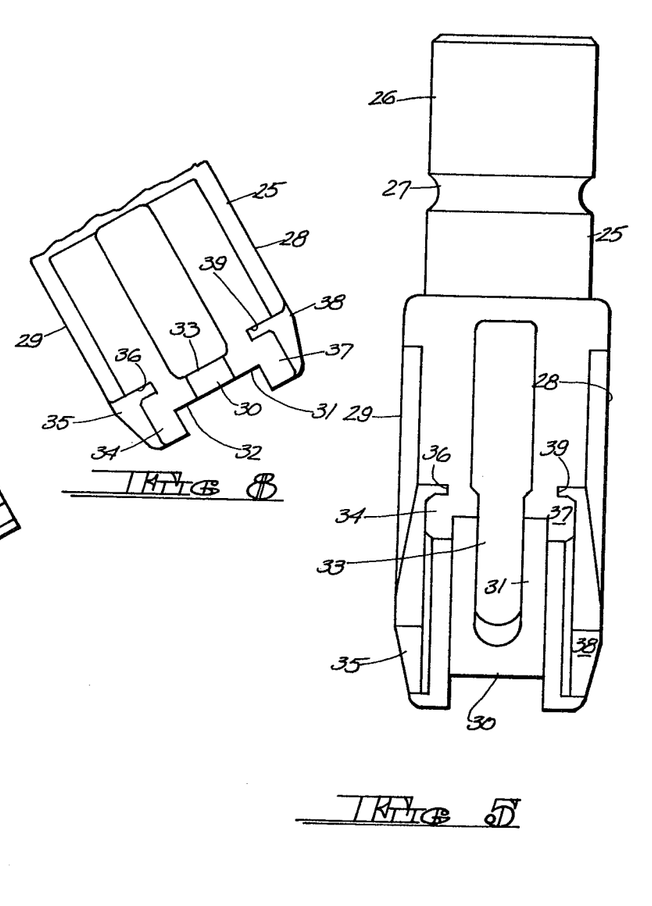
FIG. 5 is a rear elevational view of the nose casting.
FIG. 6 is a plan view of the nose casting.
Figure 6:
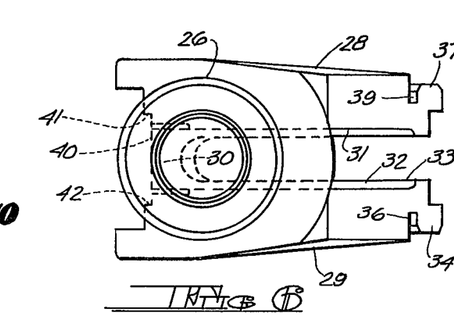
Figure 7:
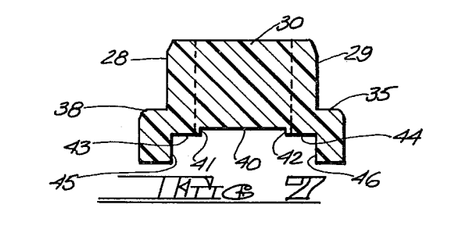
FIG. 7 is a cross sectional view taken along section lines 7—7 of FIG. 3.

Referring primarily to FIGS. 4, 5 and 8, the wall 29 has a portion of thinner dimension 34 along its bottom edge. The portion 34 extends from the rear of nose body element 25 to a stop surface 35. The portion of lesser thickness 34 is separated in part from the remainder of wall 29 by a notch 36 which extends from the rear surface of nose body element 25 downardly and forwardly to the stop surface 35.

The exterior surface of wall 28 is substantially a mirror image of the exterior surface of wall 29. To this end, wall 28 has a thinner portion 37 corresponding to the portion 34 of wall 29. The wall 28 also has a stop surface 38 corresponding to stop surface 35 and a notch 39 corresponding to notch 36.

Referring particularly to FIGS. 3, 4, 6 and 7 the forward or front end of body element 25 is provided with an inset planar surface 40 which extends from the web 30 near the bottom of body element 25 up walls 28 and 29 and along the majority of cylindrical portion 26. As is most clearly seen in FIGS. 6 and 7, the planar surface 40 is flanked by vertically extending walls or shoulders 41 and 42. The shoulders 41 and 42 are of a width slightly greater than the thickness of the driver (to be described) and they, together with the planar surface 40 and the front cover of the nose (to be described) define a driver track 40a within which the driver 6 may shift vertically.

Figures 16, 18, 19:
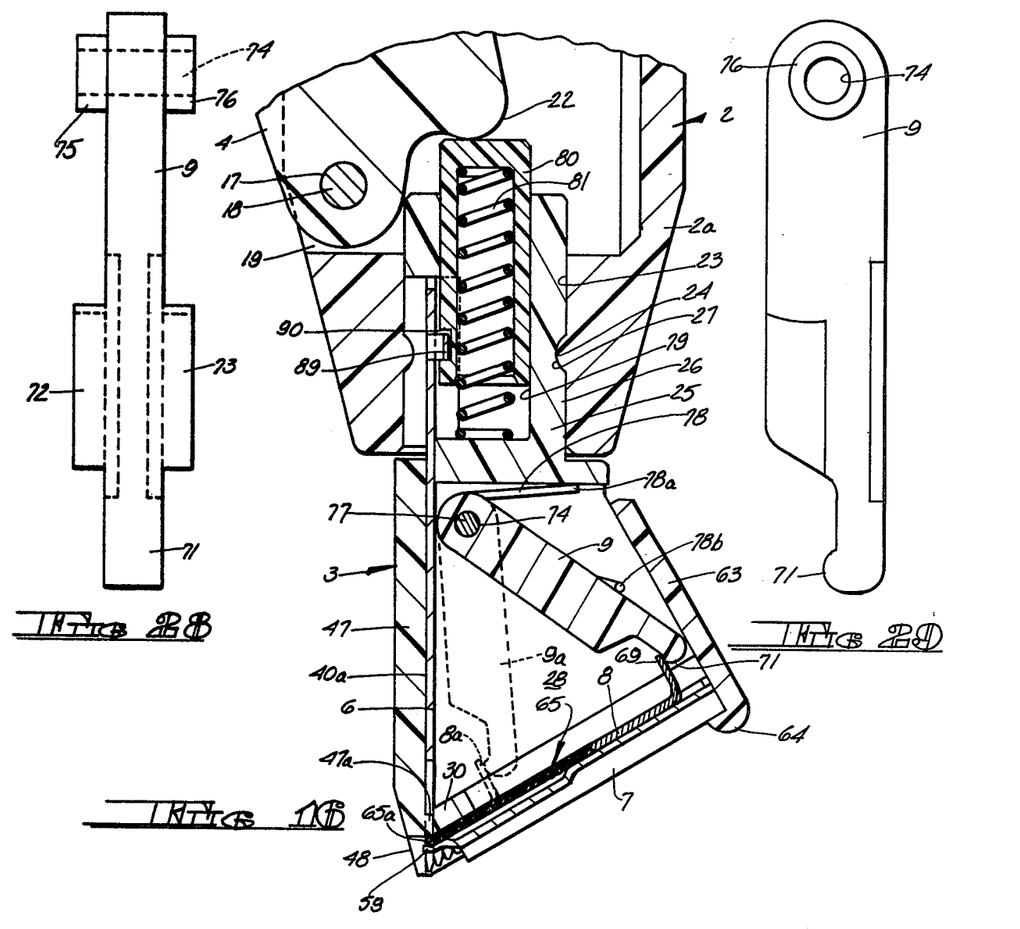
FIG. 16 is an enlarged fragmentary cross sectional view of the nose portion and the lower handle portion of the surgical instrument, illustrating the parts thereof in their normal positions.
FIG. 18 is a fragmentary elevational view, partly in cross section, of the nose portion of the instrument, illustrating a staple in fully formed condition.
FIG. 19 is a fragmentary front elevational view of the nose portion of the surgical stapling instrument.

Adjacent shoulders 41 and 42, the forward portions of walls 28 and 29 are provided with coplanar surfaces 43 and 44, these surfaces also extending upwardly along a majority of the cylindrical portion 26. The coplanar surfaces 43 and 44 are, themselves, flanked by vertical wall portions 45 and 46, respectively, formed on walls 28 and 29 and oriented perpendicular to the coplanar surfaces 43 and 44. The coplanar surfaces 43 and 44 and the flanking walls 45 and 46 define an elongated socket into which the front cover 47 of nose portion 3 is located. The front cover 47 is clearly shown in FIGS. 2, 16, 17 and 19. The cover may be molded of the same plastic material as is handle portion 2, actuator 4 and nose body element 25 and may be permanently attached to the nose body element 25 by any suitable means including welding or the like. As is shown in FIG. 19, the front cover 47 has a rectangular notch 48 formed in the bottom edge thereof through which a fully formed staple may be released from the surgical stapling instrument, again as will be described hereinafter.

Figure 9:
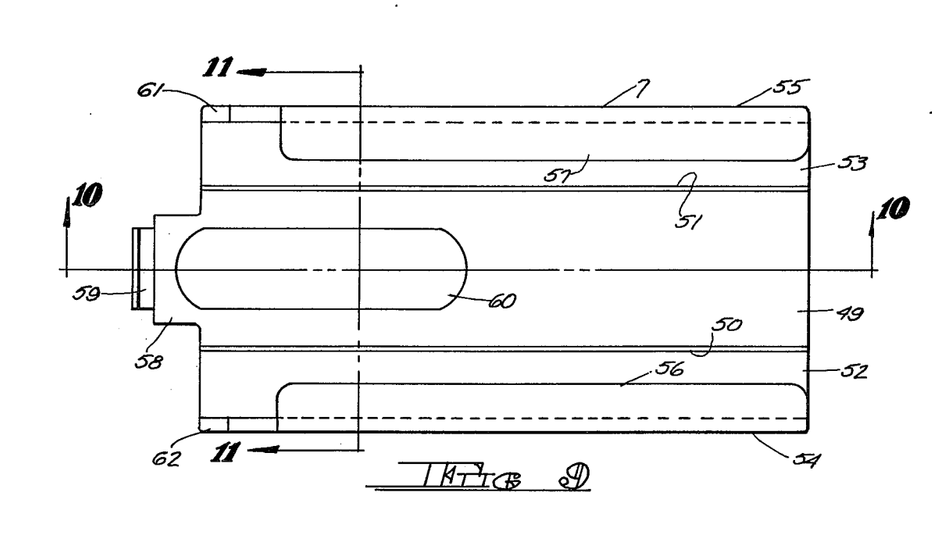
FIG. 9 is a plan view of the anvil plate of the present invention.
Figure 10:
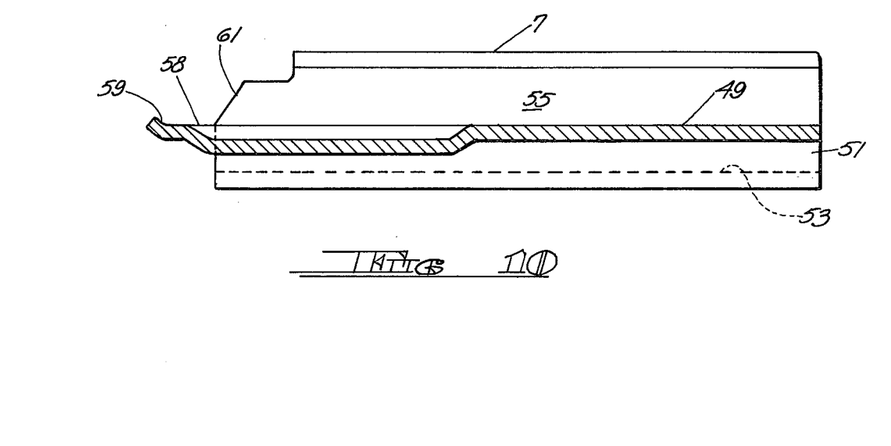
FIG. 10 is a cross sectional view taken along section line 10—10 of FIG. 9.
Figure 11:
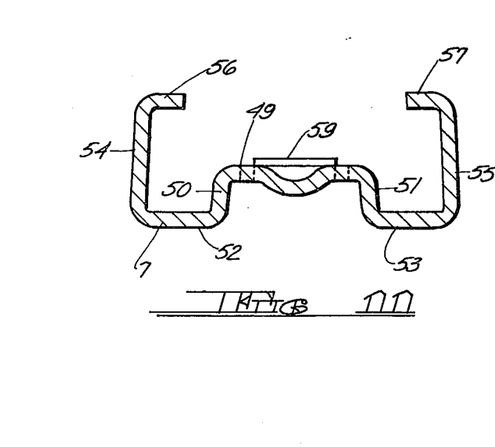
FIG. 11 is a cross sectional view taken along section 11—11 of FIG. 9.

FIGS. 9 through 11 illustrate the anvil plate 7 of the instrument. The anvil plate 7 is preferably made of metal such as stainless steel and has a longitudinal planar central portion 49. Longitudinally extending portions 50 and 51 depend downwardly from the central portion 49 to coplanar portions 52 and 53 which are parallel to central portion 49. The portions 52 and 53, in turn, are flanked by upstanding portions 54 and 55 which terminate in inturned portions 56 and 57, respectively.

The central planar portion 49 is extended as at 58 and terminates in a slightly upturned, narrower portion 59 constituting the anvil surface about which the staples are formed by the driver. The planar portion 49 may be provided with an elongated depression or dimple 60 to strengthen the structure. As is most evident from FIGS. 9 and 10, the upstanding portion or side wall 55 of the anvil plate terminates at the forward end of the anvil plate in a downwardly and forwardly sloping surface 61. The upstanding portion or side 54 of the anvil plate terminates in a similar downwardly and forwardly sloping surface 62.

A comparison of the shape of the nose body element 25 as revealed in FIG. 8 and the configuration of the anvil plate 7 as shown in FIG. 11 will make it immediately clear that the anvil plate is adapted to slip onto the bottom end of the nose body element 25 as shown in FIG. 15. Thus, inturned flange 57 of anvil plate 7 is adapted to be received in the slot 39 of wall 28. The portions 51, 53, 55 and 57 surround the narrower portion 37 of wall 28. In similar fashion, the anvil plate inturned flange 56 is adapted to be received within slot 36 of wall 29, the anvil plate portions 50, 52, 54 and 56 surrounding the narrower portion 34 of wall 29. The central planar portion 49 of the anvil plate lies in parallel spaced relationship to the interior flanges 31 and 32 of the nose body element 25. The flanges 31 and 32 are spaced above the anvil plate portion 49 by an amount slightly greater than the diameter of the staples.

When the anvil plate 7 is fully seated on the nose body element 25, the forwardly and downwardly sloping edge 62 of the anvil plate will abut the stop surface 35 of wall 29. This is illustrated in FIG. 1. In similar fashion, the downwardly and forwardly sloping edge 61 of the anvil plate will abut the stop surface 38 of wall 28. Thus, the fully seated position of the anvil plate is predetermined in such a way that the anvil surface 59 underlies the driver track and hence the driver, as will be described hereinafter. The nose body element 25 may be provided with a rear cover plate, again molded of the same material as the nose body element 25, itself. Once the anvil plate 7 is properly located on the nose body element 25 and the staples are mounted on the anvil plate, the rear cover, shown at 63 in FIGS. 1, 2, 16 and 17 may be permanently affixed to the rear of the nose body element 25 again by any appropriate means such as welding or the like. The rear cover 63 may be hooked-shaped at its bottom edge as at 64 to underlie the anvil plate 7 to assure that it is properly secured in place.

The individual staples are located in a row one-behind-the other on the anvil plate, straddling the central portion 49 thereof. As is evident from FIG. 15, the staples underlie the flanges 31 and 32 of walls 28 and 29 of the nose body element 25. The clearance between the flanges 31 and 32 and the central portion 49 of the anvil plate is such that the staples may be advanced forwardly toward the front of the surgical stapling instrument therebetween. The row of staples is generally indicated at 65 in FIGS. 16 and 17. As is most clearly shown in FIG. 16, the forwardmost staple 65a is located on the anvil forming surface 59 of anvil plate 7. Further forward movement of staple 65a is precluded by the fact that the staple, in its unformed condition, is too wide to pass through the notch 48 in the front cover 47 of the nose portion 3 (see FIG. 19). It will be noted from FIG. 16 that the front cover 47, on its rearward face has an extension 47a which is directed inwardly and is of a thickness approximating that of the staple driver. The extension 47a is spaced upwardly from the anvil forming surface 59 of anvil plate 7 by a distance approximately 25% greater than the wire diameter of the crown of the staple 65a so that it will control the amount of bending of the staple crown during the formation of staple 65a, as will be described hereinafter.

Figure 25:
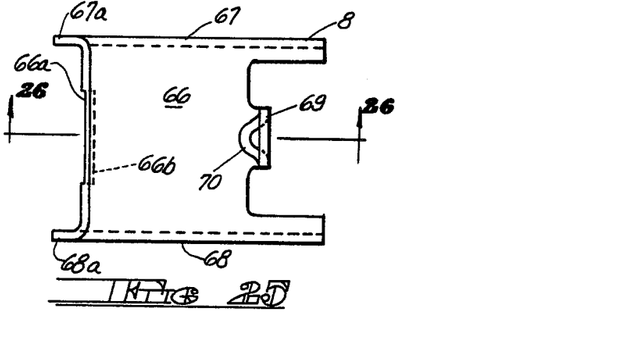
FIG. 25 is a plan view of the feeder shoe of the present invention.
Figure 26:
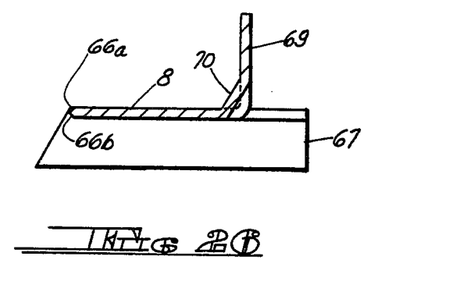
FIG. 26 is a cross sectional view taken along section line 26—26 of FIG. 25.
Figure 27:
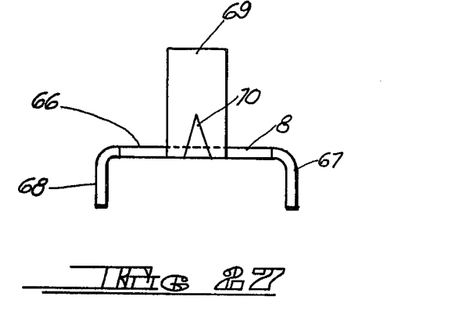
FIG. 27 is a rear elevational view of the feeder shoe.

The feeder shoe 8 and feed pawl 9 (see FIGS. 2 and 16) are provided to assure that the row of staples 65 is constantly urged toward the anvil forming surface 59 and that the staples are advanced after each staple forming operation. The feeder shoe 8 is most clearly shown in FIGS. 25 through 27. The feeder shoe comprises a planar body portion 66 with downwardly depending edge portions 67 and 68. As a consequence, the feeder shoe 8 has an inverted U-shaped configuration closely approximating the configuration of the staples themselves. The forwardmost ends of downwardly depending edge portions 67 and 68 slope downwardly and forwardly as at 67a and 68a so that the legs of the row of staples 65 will be vertically oriented and in proper position for forming when each staple reaches the anvil forming surface 59. The forwardmost edge of the planar portion 66 is similarly sloped as at 66a, but the central portion thereof is additionally provided with a reverse slope as at 66b to accommodate the anvil forming surface 59 when the feeder shoe is in its forwardmost position. The feeder shoe will straddle the central portion 49 of the anvil plate 7 as shown in FIG. 15. At its rearward edge, the planar portion 66 of the feeder shoe is provided with an integral, upstanding lug 69. A gusset 70 is formed at the juncture of lug 69 and planar surface 66 to strengthen the upstanding lug 69. Preferably, the feeder shoe 8 is made of metal such as stainless steel or the like, as is true of the anvil plate 7.

The feeder pawl 9 is illustrated in FIGS. 28 and 29. The feeder pawl comprises an elongated member the body of which has a width substantially equal to the slot 33 defined by flanges 31 and 32 of the nose body element 25 and the bottom end of the pawl is receivable therebetween. The bottom end terminates in a foot 71 adapted to contact the rear surface of the upstanding lug 69 of the feeder shoe.

On either side, the feeder pawl is provided with extensions 72 and 73 so that, at the position of these extensions, the feeder pawl will have a width substantially equal to the distance between the inside surfaces of the walls 28 and 29 of the nose body element 25. At its upper end, the feeder pawl is provided with a transverse perforation 74, surrounded on either side of the pawl by annular flanges 75 and 76. The flanges 75 and 76 together with extensions 72 and 73 will preclude lateral play of the feeder pawl within the nose portion 3 of the surgical stapling instrument. As is evident from FIG. 16, the feeder pawl is pivotally mounted within the nose portion 3, a pivot pin 77 extending through the perforation 74 in the upper end of the feeder pawl. The ends of pivot pin 77 are supported by the walls 28 and 29 of the nose body element 25. The foot portion 71 of the feeder pawl is located behind the upstanding lug 69 of feeder shoe 8. A spring 78 is mounted on pivot pin 77. One end 78a of spring 78 abuts the inside upper surface of the nose body element 25 between the walls 28 and 29 thereof. The other end 78b of spring 78 abuts the rear edge of the feeder pawl 9, so that the feeder pawl is constantly urged to pivot forwardly or clockwise, as viewed in FIGS. 2 and 16, to advance the feeder shoe 8 and hence the row of staples 65. The fully advanced positions of the feeder shoe 8 and feeder pawl 9 are shown in broken lines at 8a and 9a, respectively, in FIG. 16.

The structure thus far described is completed by the plunger and driver assembly. Reference is now made to FIG. 16. It will be noted that the upper cylindrical portion 26 of the nose body element 25 is provided with a cylindrical bore 79. A hollow cylindrical plunger 80 is slidably mounted within the bore 79. The plunger 80 is open at its lower end and closed at its upper end. The upper end is contacted by the arcuate nose 22 of actuator 4.

A compression spring 81 is located within the bore 79 of the nose portion body element 25 and within the hollow plunger 80. The upper end of spring 81 abuts the upper closed end of plunger 80 while the lower end of spring 81 abuts the bottom of bore 79 in body element 25. The spring 82 constantly urges plunger 80 upwardly and maintains contact between it and the foot 22 of actuator 4. The plunger 80 may be molded of the same plastic material as the nose portion body element 25.

Figure 12:
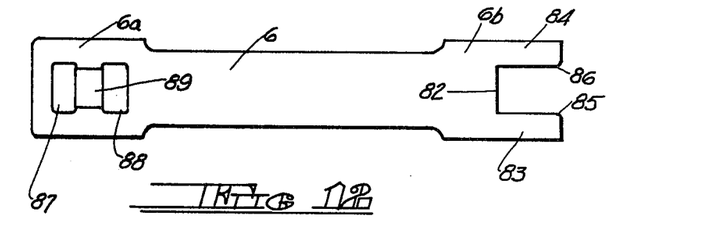
FIG. 12 is a front elevational view of the driver of the present invention.
Figure 13:
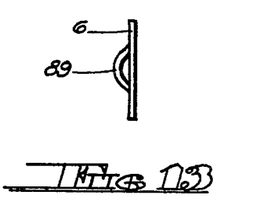
FIG. 13 is a top view of the driver of FIG. 12.

The staple driver 6 is illustrated in FIGS. 12 and 13. The driver comprises an elongated member, preferably made of metal such as stainless steel or the like. At its upper end 6a and its lower end 6b the driver is of a width to be just nicely received within driver track 40a and slidable therein. At its lower end 6b, the driver is provided with a rectangular notch 82 providing bifurcations 83 and 84 which perform the actual staple forming. The bifurcations 83 and 84 may be slightly relieved as at 85 and 86 to more readily initiate the forming action and to prevent damage to the staples.

The upper end 6a of driver 6 has a pair of perforations 87 and 88. The web 89 therebetween is deformed so as to provide a rearwardly extending dimple or lug. As is most clearly shown in FIG. 16, the lug 89 is intended to be received with a notch or depression 90 in plunger 80. The engagement of driver lug 89 in plunger notch 90 is made possible by virtue of the fact that the cylindrical portion 26 of the nose body element 25 is provided with a window or opening 91 in the forward portion of its peripheral surface. The window 91 is most clearly seen in FIG. 3.

The basic parts of the surgical stapling instrument of the present invention having been set forth, its operation may be described as follows. It will be understood that during assembly of the surgical stapling instrument, the instrument will be provided with the row 65 of staples and the entire assembly will be subjected to appropriate sterilization procedures. These procedures are well known in the art and do not constitute a part of the present invention.

The operator may adjust nose portion 3 with respect to handle portion 2 to achieve the desired rotational relationship between these elements. For example, the surgical stapling instrument may be set up as illustrated in FIG. 1 so that the handle portion 2 and the hand of the operator will be essentially parallel to the wound or incision being closed and will be drawn therealong. Alternatively, the operator my prefer to orient the handle and his hand at an angle to the length of the wound or incision. This will, of course, depend upon the nature of the wound or incision, its location on the body of the patient and the personal preference of the operator.

Figure 14:
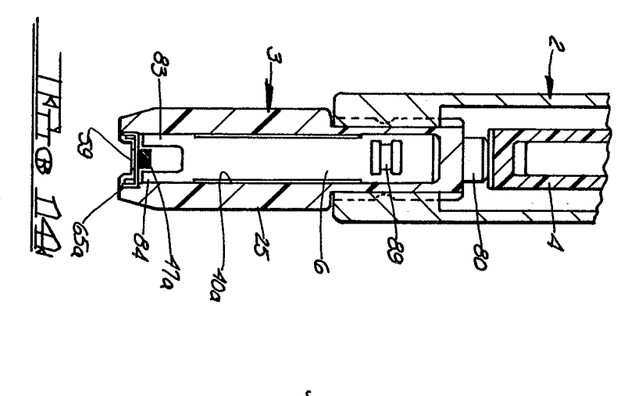
FIG. 14 is a fragmentary cross sectional view taken along section line 14—14 of FIG. 2.

FIGS. 1, 2 and 16 illustrate the surgical stapling instrument in its normal, unactuated condition. The compression spring 81 within plunger 80 will urge plunger 80 upwardly. This, in turn, will urge actuator 4 in a counter clockwise direction (as viewed in those figures) about pivot pin 18. The uppermost position of plunger 80 and the normal position of actuator 4 are determined by the abutment of actuator foot 16 against the inside surface of handle portion 2, at the upper end of opening 10 in the handle portion. With plunger 80 in its uppermost position, the driver 6 will also be in its uppermost position. It will be noted from both FIGS. 14 and 16 that, when the plunger is in its uppermost position it is still spaced slightly from the uppermost end of driver track 40a.

The row of staples 65 will be constantly urged toward the anvil forming surface 59 by feeder shoe 8 and feeder pawl 9 under the influence of spring 78. It will be evident that when the surgical stapling instrument of the present invention is in its normal position, there will always be a staple (until row 65 is depleted) located upon the anvil forming surface 59 and beneath the staple retainer 47a on the front closure 47 of the nose portion 3. The forwardmost staple 65a is illustrated in this position in FIG. 14. The fowardmost staple 65 will maintain this position by virtue of the fact that, in its unformed condition, it is too wide to pass through the rectangular notch 48 in front cover 47 (as shown in FIG. 19). Of particular importance is the fact that the staples in the row 65 thereof are always supported on the anvil plate and no transfer of the staples from a cartridge or the like is required. The advancement of the row 65 of staples is wholly independent from the staple driver 6 and the mechanism which actuates it. As a consequence of this, less force is required to actuate the surgical stapling instrument of the present invention and all of the force applied to the actuator is utilized to form the implant the forwardmost staple 65a. This further reduces the length of the stroke required of actuator 4.

Figure 17:
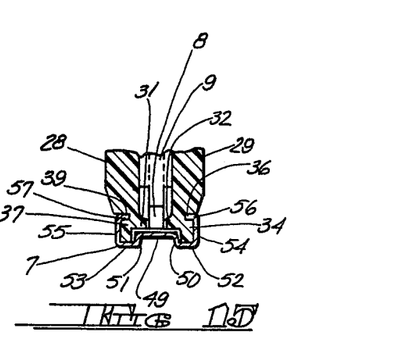
FIG. 17 is a fragmentary cross sectional view similar to FIG. 16 and illustrating the parts in their respective positions immediately after the forming of a staple.
Figure 18:
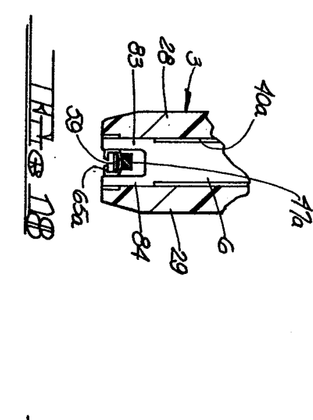
Figure 19:
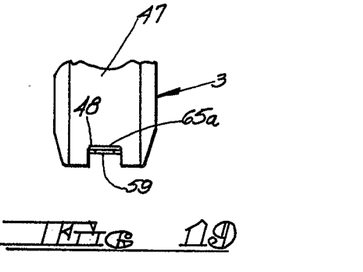

Once the sides of the wound or incision have been properly gathered at the position where a staple is to be implanted, the lower front portion of the nose 3 of the instrument is located on that position and the actuator 4 is shifted in the direction of arrow A in FIG. 1. This clockwise pivoting of the actuator (as viewed in FIGS. 1, 2 and 16) about pivot pin 18 will cause the arcuate foot 22 of the actuator to depress plunger 80 against the action of compression spring 81. This downward movement of plunger 80 will simultaneously cause a downward movement of driver 6 (see FIG. 17). As will be evident from a comparison of FIGS. 14 and 16 and FIGS. 17 and 18, the downward movement of driver 6 will cause its bifurcations 83 and 84 to engage the outermost portions of the crown of staple 65a and will bend these portions about the staple forming surface 59 of anvil plate 7. As a result, the original downwardly depending portions of forwardmost staple 65a will enter the skin or fascia of the patient and at the same time approach each other, gathering the skin or fascia together. The final shape of the staple at the end of the stroke of the driver 6 is illustrated in FIGS. 17 and 18. The central crown portion of the formed staple will bow slightly, but the amount of this bow is controlled and minimized by the staple retainer lug 47a. A comparison of FIGS. 18 and 19 will reveal that the formed staple is now of a size and configuration such that it may pass through the rectangular notch 48 in the front closure 47 of nose portion 3. Upon retraction of driver 6 to its upper position shown in FIGS. 14 and 16, the tendency of the staple legs to spread until the staple crown is relieved of its bow and the action of feeder shoe 8 and feeder pawl 9 will cause the formed staple 65a to be released from between the anvil forming surface 59 and staple retainer lug 47a. The released staple passes readily through the rectangular notch 48 in the front cover 47 of nose portion 3.

Upon release of manual pressure urging the actuator in the direction of arrow A in FIG. 1, the compression spring 81 will be free to shift the plunger 80 upwardly. This, in turn, will pivot the actuator in a direction opposite that indicated by arrow A of FIG. 1 to its normal, unactuated position as determined by actuator foot 16. The upward movement of the plunger will also shift the staple driver upwardly. Upon release of the formed staple from between the staple retainer lug 47a and the anvil forming surface 59 of anvil plate 7, the next staple in the row 65 thereof will shift to its ready position between anvil surface 59 and staple retainer lug 47a so that the stapling operation can be repeated at the will of the operator.

It is within the scope of the present invention to provide a safety latch means for the actuator, to prevent inadvertent operation of the surgical stapling instrument. Reference is now made to FIGS. 1, and 20 through 24, wherein an exemplary safety latch means is illustrated. As is most clearly shown in FIGS. 21 and 23, the handle half 2b may be provided on its interior surface with an enlarged boss 91 located at the forward end of the internal reinforcing rib 21 and near the opening 10 in the forward edge of the handle half. The enlarged boss has a perforation 92 extending therethrough. The perforation 92 has a portion 93 of enlarged diameter. A push button 94 is located in the perforation 92. The push button has an annular flange 95 at its rearward end which is accommodated in the enlarged diameter portion 93 of perforation 92 (see FIG. 21). The boss 91 also has a notch 96 formed therein. The notch 96 intersects the large diameter portion 93 of the perforation 92.

Figure 24:
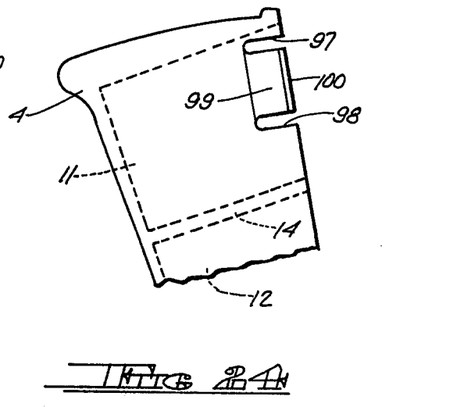
FIG. 24 is a fragmentary elevational view of the actuator illustrating another portion of the latch means.

Turning now to FIG. 24, the side of the actuator 4 which lies adjacent handle half 2b is provided with a pair of spaced notches 97 and 98. Between notches 97 and 98 there is a web 99 of lesser thickness than the normal wall thickness of the wall actuator, the web 99 terminates in a hook-like element 100.

Figure 21:
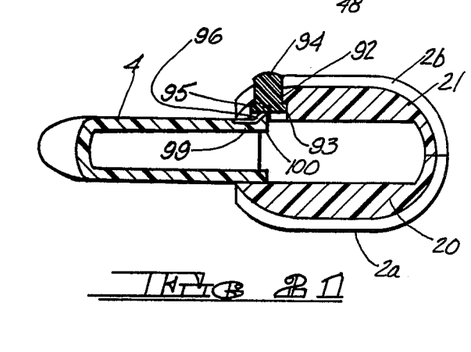
FIG. 21 is a cross sectional view taken along section line 21—21 of FIG. 1.

FIG. 21 illustrates the handle portion 22 with the actuator 4 in its normal position. It will be immediately evident that the button 94 is captive in perforation 92 since the flange portion 95 of the button is of greater diameter than the perforation 92 and since the button will be retained within perforation 92 by actuator 4. With the actuator 4 in its normal position as illustrated in FIG. 21, the hook-like element 100 is engaged in the notch 96 of boss 91. This engagement will maintain the actuator in its normal position.

Figure 22:
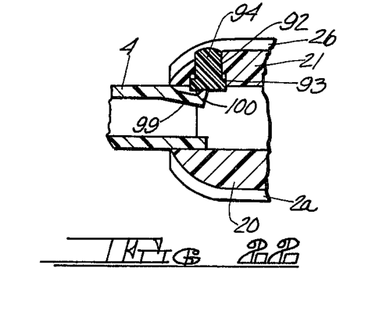
FIG. 22 is a fragmentary cross sectional view similar to that of FIG. 21 and illustrating the latch means in its unlatched condition.

When the surgical stapling instrument is to be actuated, the operator will grasp the handle portion 2 in such a way as to depress button 94. This, in turn, will lift the hook-like element 100 out of notch 96 through a bending action of the web 99. Once this is done, the actuator 94 is free to be shifted to its working position resulting in the implanting and forming of a staple. During this movement of the actuator, the hook-like element 100 will simply ride along the edge of the rib 21 of handle half 2b. When the actuator returns to its normal position it will not be locked so long as the button 94 is maintained in its depressed position as illustrated in FIG. 22. Should the button 94 be released by the operator, however, the actuator will be latched as shown in FIG. 21.

The surgical stapling instrument of the present invention has been described in its form as a single-use, disposable instrument. Under these circumstances, only springs 78 and 81, anvil plate 7 feeder shoe 8 and driver 6 are made of metal. The driver 6, anvil plate 7 and feeder shoe 8 are preferably made of stainless steel. The remainder of the structure may be made, as indicated above, of any appropriate plastic material having sufficient strength characteristics and capable of withstanding appropriate sterilization procedures. Excellent results have been achieved, for example, when these remaining parts of the surgical stapling instrument have been molded of nylon, polysulfone, or the like. The surgical stapling instrument may, of course, be manufactured as a non-disposable instrument, the parts being made of appropriately selected materials. In such an instance, the rear cover 63 of nose portion 3 should be made removable and preferably the front cover 47 will also be removable. The covers 63 and 47 may be affixed to the nose body element 25 under these circumstances by screws or the like. This would enable the various parts to be replaced and repaired and an additional supply of staples to be located on anvil plate 7.

While the surgical stapling instrument of the present invention has been described and illustrated as utilizing conventional surgical staples, the device may readily be modified to utilize surgical staples of the type taught in U.S. Pat. No. 4,014,492. Under these circumstances, it would only be necessary to modify the configuration of the inside surfaces of the portions 34 and 37 of the legs 29 and 28 of nose body element 25 and the undersides of the nose body element flanges 31 and 32 to accommodate staples of that configuration. In all other respects, the surgical stapling instrument of the present invention would be and would operate as described above.

Modifications may be made in the invention without departing from the spirit of it.

The embodiments of the invention in which an exclusive property or privilege is claimed are defined as follows:

1. A surgical stapling instrument for forming and implanting a staple in the skin or fascia of a patient, said instrument comprising a handle portion incorporating a nose portion, said nose portion having an anvil plate at the bottom end thereof, said anvil plate terminating at its forward end in a coextensive anvil surface, said anvil plate being adapted to slidably mount a row of staples, means to constantly urge and advance said row of staples along said anvil plate to place a forwardmost staple of said row on said anvil surface, a staple driver mounted in said nose portion and shiftable vertically between a normal upper position closely adjacent said forwardmost staple on said anvil surface and a lower position wherein it forms and implants said forwardmost staple about said anvil surface, and means to shift said staple driver between said upper and lower positions thereof.

2. The structure claimed in claim 1, wherein said means to constantly urge and advance said row of staples along said anvil plate is independent of said means to shift said staple driver.

3. The structure claimed in claim 1 wherein said nose portion is rotatable through 360° with respect to said handle portion whereby said surgical stapling instrument may be used in various attitudes.

4. The structure claimed in claim 1 including releasable latch means to prevent inadvertant actuation of said means to shift said staple driver.

5. The structure claimed in claim 1 including staple retaining means overlying said anvil surface to control the amount of bending of the crown portion of the staple being formed by said staple driver.

6. The structure claimed in claim 5 wherein said means to constantly urge and advance said row of staples along said anvil plate toward said anvil surface is independent of said means to shift said staple driver.

7. The structure claimed in claim 5 wherein said staple retaining means is spaced upwardly from said anvil surface by a distance about 25% greater than the wire diameter of said staples.

8. The structure claimed in claim 5 including a plunger mounted in said nose portion and shiftable vertically therein between a normal upper position and a lower position, means to urge said plunger to said normal upper position, said staple driver being operatively connected to said plunger, said normal upper position of said plunger corresponding to said normal upper position of said driver, said lower position of said plunger corresponding to said lower position of said staple driver, an actuator pivotally mounted on said handle portion to shift said plunger and hence said staple driver between their respective upper and lower positions.

9. The structure claimed in claim 8 wherein said nose portion comprises a body element having a cylindrical portion rotatively mounted in said handle portion and a pair of downwardly depending walls in parallel spaced relationship, forward portions of said walls providing a vertical driver track within which said driver is slidably mounted, said anvil plate being affixed to the bottom edges of said walls with said anvil surface underlying said driver track, said anvil plate having a longitudinally extending raised certral portion located between said walls and leading to said anvil surface, said walls each having an internal flange partially overlying said raised central portion of said anvil plate and in parallel spaced relatinship thereof, said staples of said row thereof straddling said raised central portion of said anvil plate beneath said wall flanges, said body element having a rear cover extending across the rear edges of said walls and a front cover closing the space between said walls at the front edges thereof, said front cover having a notch at the bottom thereof so dimensioned that the forwardmost staple of said row can pass therethrough only after being formed by said driver, said front cover having a lug extending inwardly between said walls for a distance approximating the thickness of said driver and constituting said staple retaining means, said cylindrical portion of said body element having an axial bore formed therein, said plunger comprising a hollow cylindrical element open at its bottom end and closed at its top end and slidably mounted in said bore, a compression spring mounted within said plunger to urge said plunger to said normal upper position, one end of said compression spring abutting the bottom of said bore end the other end of said compression spring abutting the closed top end of said plunger.

10. The structure claimed in claim 9 wherein said staple retaining means is spaced upwardly from said anvil surface by a distance about 25% greater than the wire diameter of said staples.

11. The structure claimed in claim 9 including a feeder shoe straddling said raised central portion of said anvil plate and slidably mounted thereon behind said row of staples, a feeder pawl pivotally mounted between said nose body element walls, spring means urging said feeder pawl against said feeder shoe to urge and advance said row of staples along said anvil plate toward said anvil surface.

12. The structure claimed in claim 10 wherein said handle portion is hollow with an opening in the forward edge thereof, said actuator comprising an elongated member pivoted at its lower end to said handle portion and swingable between a normal position wherein the majority of said actuator is located outside said handle portion and a working position wherein the majority of said actuator lies within said handle portion, the lower end of said actuator having an extension in abutting relationship with said top end of said plunger, said actuator being biased to said normal position by said compression spring and said abutting relationship of said top end of said plunger and actuator extension, said actuator extension being so configured and positioned that when said actuator is shifted to its working position, said extension will shift said plunger to its lower position and hence said driver to its staple forming position against the action of said compression spring.

13. The structure claimed in claim 12 including a latch means for said actuator to maintain said actuator in its normal position unless released, said latch means comprising a resilient tyne on said actuator, a notch on the inside surface of said handle portion to receive said tyne when said actuator is in said normal position and pushbutton means on said handle portion to remove said tyne from said notch to release said actuator.

14. The structure claimed in claim 12 wherein said anvil plate feeder shoe, driver, feeder pawl spring means and compression spring are formed of metal, the remainder of said surgical stapling instrument being formed of plastic material.

* * * * *